US00PP10062P

Jnited States Patent [19]

kerboom

[11] Patent Number: Plant 10,062

[45] Date of Patent: Oct. 14, 1997

4] ASTER PLANT NAMED 'RED MONARCH'

5] Inventor: Petrus J. Akerboom, Ter Aar, Netherlands

3] Assignee: De Nachtvlinder B.V., Ter Aar, Netherlands

1] Appl. No.: 663,457

2] Filed: Jun. 3, 1996

1] Int. Cl.[6] ..... A01H 5/00

2] U.S. Cl. ..... Plt./68.1

8] Field of Search ..... Plt./68.1

*Primary Examiner*—James R. Feyrer
*Assistant Examiner*—Kent L. Bell
*Attorney, Agent, or Firm*—C. A. Whealy

[57] ABSTRACT

A distinct cultivar of Aster plant named Red Monarch, characterized by its moderately vigorous growth rate; freely branching plant habit; small daisy-type inflorescences; red purple ray florets; numerous inflorescences per plant; and good container and garden performance.

2 Drawing Sheets

1

The present invention relates to a new and distinct cultivar Aster plant, botanically known as Aster L. and referred to the cultivar name Red Monarch.

The new cultivar is a product of a planned breeding ogram conducted by the inventor in Ter Aar, The Nether- nds. The objective of the breeding program was to create w Aster cultivars having desirable inflorescence colors d good container and garden performance.

The new cultivar is a spontaneous mutation of the com- ercial cultivar Purple Monarch, disclosed in U.S. Plant Pat. o. 8,387. The new cultivar was discovered and selected by e inventor in a controlled environment in Ter Aar, The etherlands, as a single flowering plant among a population plants of the parent cultivar Purple Monarch. This single ant consistently formed inflorescences having red purple y florets compared to the blue purple-colored ray florets of ants of the cultivar Purple Monarch.

Asexual reproduction of the new cultivar by terminal ttings taken at Ter Aar, The Netherlands, has shown that e unique features of this new Aster are stable and repro- ced true to type in successive generations.

The following traits have been repeatedly observed and e determined to be the unique characteristics of Red onarch. These characteristics in combination distinguish ed Monarch as a new and distinct cultivar:

1. Moderately vigorous growth rate.
2. Freely branching plant habit.
3. Small daisy-type inflorescences.
4. Red purple ray florets.
5. Numerous inflorescences per plant.
6. Good container and garden performance.

The cultivar Red Monarch has not been observed under l possible environmental conditions. The phenotype may ary somewhat with variations in environment such as mperature, daylength and light intensity, without, how- ver, any variance in genotype.

Plants of the new Aster can be compared to the parent ltivar, Purple Monarch. In side-by-side comparisons con- cted in Ter Aar, The Netherlands, under commercial actice, plants of the new Aster differed from plants of the arent cultivar, Purple Monarch, in ray floret color and eight. Plants of the new Aster have red purple-colored ray orets whereas plants of the cultivar Purple Monarch have lue purple-colored ray florets. Plants of the new Aster are ller than plants of the cultivar Purple Monarch.

The accompanying colored photographs illustrate the verall appearance of the new cultivar, showing the colors as ue as it is reasonably possible to obtain in colored repro- uctions of this type.

2

The first photograph comprises a top perspective view of typical inflorescences of the new Aster.

The second photograph comprises a top perspective view of a typical plant of the new Aster (left) and the parent cultivar 'Purple Monarch' (right). The ray floret and foliage colors in these photographs vary from the actual ray and foliage colors due to light reflectance.

In the following description, color references are made to The Royal Horticultural Society Colour Chart except where general terms of ordinary dictionary significance are used. The following observations and measurements describe plants grown in Salinas, Calif., and Ter Aar, The Netherlands. Measurements and numerical values represent ranges or averages for four typical flowering plants.

Botanical classification: Aster L. cultivar Red Monarch.

Commercial classification: Garden or container Aster.

Parentage: Spontaneous mutation of the cultivar Purple Monarch, disclosed in U.S. Plant Pat. No. 8,387.

Propagation:

*Type.*—Terminal tip cuttings.

*Time to rooting.*—Summer: About 6 days at 25C soil temperature. Winter: About 10 days at 15C soil temperature.

*Rooting habit.*—Fine, fibrous and well-branched.

Plant description:

*Appearance.*—Perennial herbaceous decorative container or garden plant. Stems upright, uniform habit and freely branching. Moderately vigorous and compact growth habit.

*Plant height.*—17 to 22 cm.

*Lateral branch length.*—8 to 10 cm.

*Quantity of lateral branches after removal of apical meristem.*—Usually 3.

*Stem color.*—147A.

*Foliage description.*—Number of leaves per lateral branch: Usually 9 to 10. Leaf arrangement: Alternate. Leaf size, leaves from vegetative plants: Length: About 12 cm. Width: About 2.5 cm. Leaf size, leaves from flowering plants: Length: About 3.5 cm. Width: About 8 mm. Leaf apex: Acuminate. Leaf base: Attenuate. Leaf margin: Leaves from vegetative plants: Serrate. Leaves from flowering plants: Entire. Leaf texture: Glabrous, dull, leathery. Color: Young foliage upper surface: 147A. Young foliage under surface: 147B. Fully expanded foliage upper surface: 147A. Fully expanded foliage under surface:

147B. Venation upper surface: 147B. Venation under surface: 147B.

Flowering description:

*Appearance.*—Daisy inflorescence form. Inflorescences borne on terminals above foliage, arising from leaf axils. Disc and ray florets arranged acropetally on a capitulum.

*Flowering rsponse.*—Under natural conditions, plant flower in the autumn/winter in the Northern Hemisphere. At other times of the year, inflorescence initiation and development can be induced under short day/long night conditions.

*Quantity of inflorescences.*—Inflorescences form at every leaf axil. Usually 9 to 10 inflorescences per flowering stem.

*Inflorescence size.*—Diameter: About 3 cm. Depth (height): About 1 cm. Diameter of disc: About 8 mm.

*Ray florets.*—Shape: Long, narrow. Size: Length: About 1.1 cm. Width: About 3 mm. Apex: Obtuse. Base: Attenuate. Margin: Entire. Texture: Satiny, smooth and glabrous. Aspect: Flat. Number of ray florets per inflorescence: About 30. Color: When opening, upper surface: 77C. When opening, under surface: 77D. Mature, upper surface: 77A, fading to 77B/77C with subsequent development. Mature, under surface: 77C.

*Disc florets.*—Shape: Fluted, cylindrical. Size: Length: About 7 mm. Width: About 1 mm. Number of disc florets per inflorescence: About 30. Color: Immature: 1A. Mature: 9C.

*Peduncle.*—Aspect: Strong and angled about 45° to the stem. Length: About 5 cm. Texture: Glabrous. Color: 147A.

*Reproductive organs.*—Androecium: Present on disc florets only. Anther color: 9C. Pollen: Small amount, 9C in color. Gynoecium: Present on both ray and disc florets. Style color: 154C.

Disease resistance: No known Aster diseases observed to date on plants grown under commercial greenhouse conditions.

Seed production: Seed production has not been observed.

It is claimed:

1. A new and distinct cultivar of Aster plant named Red Monarch, as illustrated and described.

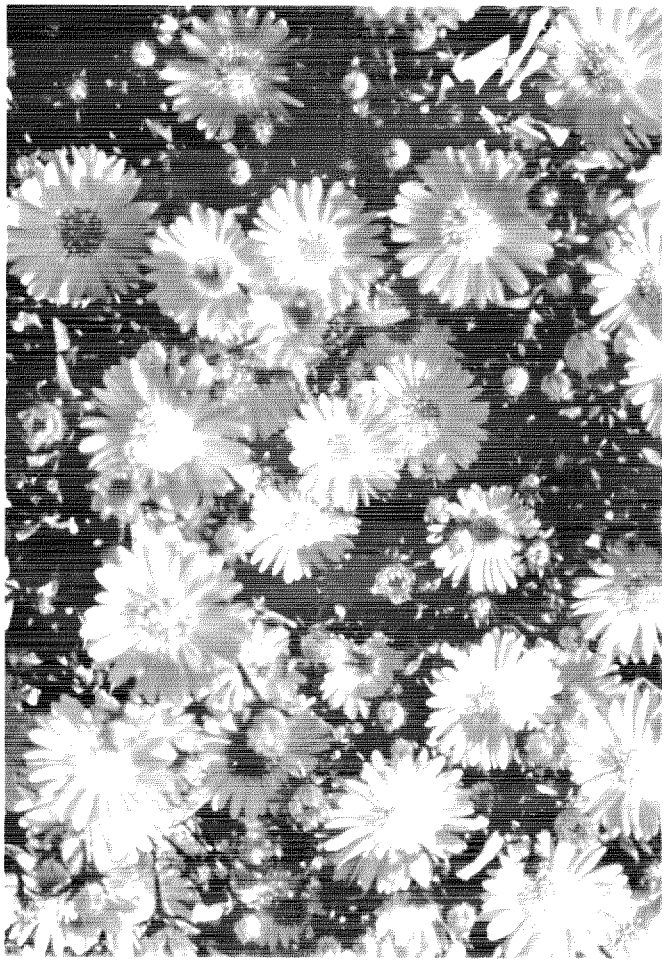

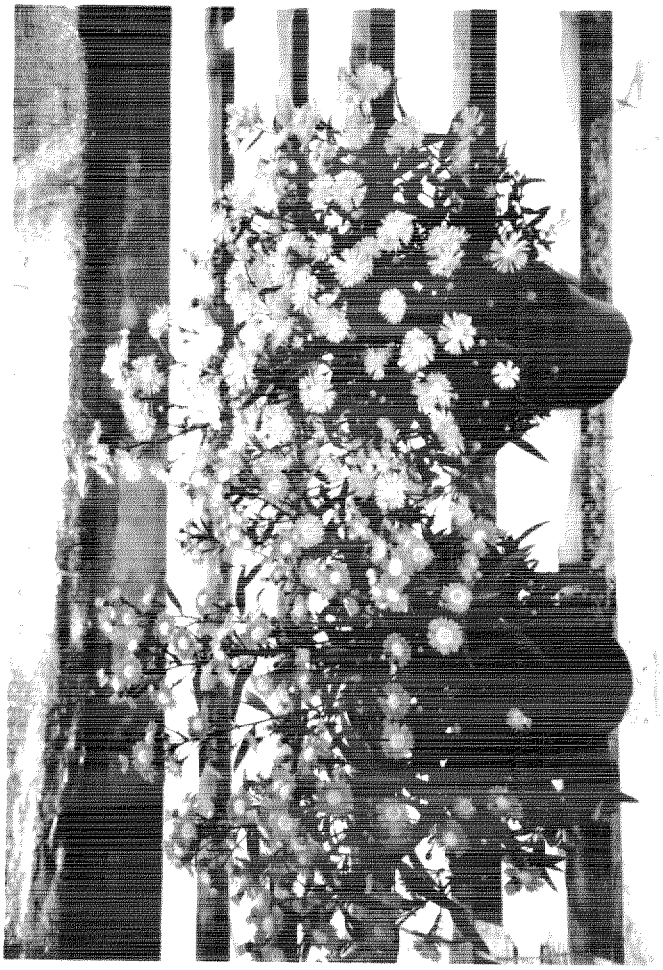

* * * * *